(12) United States Patent
Schmitt et al.

(10) Patent No.: US 9,017,706 B2
(45) Date of Patent: Apr. 28, 2015

(54) CORE-SHELL MATERIAL, METHOD FOR PREPARING SAME, AND USE THEREOF FOR THE THERMOSTIMULATED GENERATION OF SUBSTANCES OF INTEREST

(75) Inventors: Véronique Schmitt, Talence (FR); Mathieu Destribats, Bordeaux (FR); Rénal Backov, Bordeaux-Cauderan (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/387,758

(22) PCT Filed: Jul. 28, 2010

(86) PCT No.: PCT/FR2010/051604
§ 371 (c)(1),
(2), (4) Date: Jan. 30, 2012

(87) PCT Pub. No.: WO2011/012813
PCT Pub. Date: Feb. 3, 2011

(65) Prior Publication Data
US 2012/0128747 A1    May 24, 2012

(30) Foreign Application Priority Data
Jul. 31, 2009   (FR) ..................................... 09 55417

(51) Int. Cl.
*A61K 8/02* (2006.01)
*C04B 14/04* (2006.01)
*B01J 13/18* (2006.01)

(52) U.S. Cl.
CPC ........................................ *B01J 13/18* (2013.01)

(58) Field of Classification Search
None
See application file for complete search history.

(56) References Cited

FOREIGN PATENT DOCUMENTS

| FR | 2865416 | * | 1/2004 | ................ B01F 3/08 |
| FR | 2865416 | | 7/2008 | |
| WO | 2008072239 | | 1/2004 | |

OTHER PUBLICATIONS

Machine Translation of FR 2865416, accessed May 9, 2013, pp. 1-14.*
International Search Report dated Oct. 26, 2010.

* cited by examiner

*Primary Examiner* — Trevor Love
(74) *Attorney, Agent, or Firm* — Sofer & Haroun, LLP

(57) ABSTRACT

The present invention relates to a material in the form of solid particles consisting of a continuous shell including at least one silicon oxide, said shell confining at least one oil phase, said material being characterized in that said oil phase is solid at the storage temperature of said material and predominately contains a crystallizable oil that has a melting temperature ($T_M$) of less than 100° C. and at least one substance of interest, and in that the diameter of the particles varies from 1 μm to 1 cm. The invention also relates to a method for preparing said material, to the use thereof for the thermostimulated generation of active substances, as well as to compositions containing same.

12 Claims, 8 Drawing Sheets

CORE-SHELL MATERIAL, METHOD FOR PREPARING SAME, AND USE THEREOF FOR THE THERMOSTIMULATED GENERATION OF SUBSTANCES OF INTEREST

RELATED APPLICATIONS

This application is a National Phase application of PCT/FR2010/051604, filed on Jul. 28, 2010, which in turn claims the benefit of priority from French Patent Application No. 09 55417 filed on Jul. 31, 2009, the entirety of which are incorporated herein by reference.

BACKGROUND

1. Field of the Invention

The present invention relates to a material constituted of a silica shell containing a wax core, to the process for preparing the same, to the use thereof for the thermostimulated delivery of active substances, and also to the compositions containing such a material.

2. Description of Related Art

It may be useful to encapsulate molecules of interest such as medicaments, dyes, pigments, reactants, fragrances, pesticides, etc., in order to protect them from outside attacks, especially oxidation, in order to convey them to a site of administration where they will be able to be delivered or else in order to store them before use under conditions where they will be released from their capsule under the influence of an external stimulus. One of the first applications of microencapsulation was the development of a carbonless copy paper sold at the end of the 1960s in which microcapsules comprising an ink were present on the back of a sheet of paper so as to release the ink by rupture of the capsules under the pressure exerted by the tip of a pen when writing. These days, encapsulation is expanding in various industrial sectors such as the pharmaceutical, cosmetic, food, textile and agricultural industries. The capsules and microcapsules are becoming increasingly sophisticated, especially in the pharmaceutical field where they make it possible to carry out controlled and/or targeted delivery of active principles.

Various types and morphologies of capsules and microcapsules have already been proposed such as, for example, protein capsules, cyclodextrins, liposomes, concentrated lamellar vesicles, double emulsions, colloidosomes, microcapsules, silica nanocapsules and heat-sensitive polymers such as poly(N-isopropylacrylamide (PNIPAM), heat-sensitive hydrogel microspheres, microspheres of PNIPAM-polylactide, etc. Numerous methods that make it possible to prepare these various types of capsules and microcapsules have also been expanded and developed during recent years, such as, for example and nonexhaustively, the precipitation of polymers by phase separation, layer-by-layer electrolyte deposition, polymerization by interfacial polycondensation, etc.

OBJECTS AND SUMMARY

The drawback of the already-known techniques is that the release of the molecules of interest from the capsules and microcapsules proposed in the prior art is usually slow and gradual, that is to say prolonged over time.

To date, no system exists that allows a rapid and complete release of molecules of interest under the effect of an external stimulus under mild conditions.

The objective of the present invention is therefore to propose a capsule that makes it possible to encapsulate one or more molecules of interest which may be released rapidly and completely under the influence of an external stimulus, and in particular an increase in the temperature.

One subject of the present invention is a material in the form of solid particles constituted of a continuous shell comprising at least one silicium oxide, said shell comprising at least one fatty phase, said material being characterized in that said fatty phase is solid at the storage temperature of said material and predominantly comprises a crystallizable oil having a melting point ($P_M$) below 100° C. and at least one substance of interest, and in that the diameter of said particles varies from 1 .mu.m to 1 cm.

According to the present invention, the expression "storage temperature of said material" is understood to mean the temperature at which the material in accordance with the present invention is kept before the use thereof. This temperature is always below the melting point of the crystallizable oil contained in the fatty phase.

The material in accordance with the present invention exhibits the following distinctive feature: when the material is subjected to a temperature above the melting point of the crystallizable oil, a thermal expansion of the fatty phase is observed that leads to the rupture of the silica shell and the rapid and complete release of the molten fatty phase (i.e. fatty phase in the liquid state) comprising the substance or substances of interest. This result is quite surprising insofar as the silicium oxide that is incorporated into the composition of the shell is known for being a thermal insulator.

Within the context of this document, the expression "crystallizable oil" is understood to mean fatty substances and mixtures of fatty substances, of natural (animal or plant) or synthetic origin, the melting point of which is above 15° C., preferably the melting point of which varies from 20 to 100° C. approximately and in particular from 20 to 50° C. approximately. All of the melting points mentioned in the description of the present application refer to melting points determined by Differential Scanning calorimetry (DSC) at atmospheric pressure.

The crystallizable oil forms a predominant portion of the fatty phase and may even, besides the substances of interest, be the sole constituent thereof. Generally, the crystallizable oil represents 50% to 99.9% by weight approximately, preferably from 75% to 99.9% by weight approximately of the fatty phase.

The choice of the crystallizable oil naturally depends on the application envisaged for the material and therefore on the temperature at which it is desired to observe the thermal expansion of the fatty phase and consequently the rupture of the silica shell. Among the crystallizable oils that can be used according to the invention, mention may especially be made of paraffins such as the paraffins having a melting point between 42 and 44° C. or between 46 and 48° C. [RN: 8002-74-2] sold by the company Merck; triglycerides; fatty acids; rosins; waxes (long alkanes) such as eicosane and octadecane; hydrogenated plant oils and also mixtures thereof; and synthetic bitumens. These oils may be used alone or as mixtures.

The material in accordance with the present invention is preferably in the form of a powder of spherical or substantially spherical particles.

The diameter of the particles preferably varies from 5 μm to 500 μm approximately, and more preferably still from 10 to 200 μm.

The silica shell must have a thickness that is sufficient to have a mechanical strength that allows the encapsulation of the fatty phase, while being thin enough to be able to break during a rise in temperature to a temperature above the melting point of the fatty phase constituting the core of the material. The thickness of the silica shell generally varies from 0.1 to 2 µm approximately, and preferably from 0.2 to 2 µm approximately.

In addition to the silicon oxide, the shell may in addition comprise one or more metal oxides of formula $MeO_2$ in which Me is a metal chosen from Zr, Ti, Th, Nb, Ta, V, W and Al. In this case, the shell is a mixed matrix of $SiO_2$-$MeO_2$ type in which the content of $MeO_2$ remains in the minority relative to the content of silicon oxide, preferably the content of $MeO_2$ represents from 1% to 40% by weight, more particularly from 5% to 30% by weight relative to the total weight of the shell.

The fatty phase of the material in accordance with the invention may contain any type of substances of interest, whether these are lipophilic or hydrophilic. Thus, when the substance or substances of interest are lipophilic, the fatty phase contains them in solubilized form and when the substance or substances of interest are hydrophilic, the fatty phase contains them in dispersed form (directly in the crystallizable oil or in a fraction of water dispersed within the fatty phase (double emulsion)). It is also possible for them to be solid particles.

Among the substances of interest that may be incorporated into the fatty phase of the material in accordance with the present invention, mention may especially be made of medicaments (active principles), active principles that can be used in cosmetics, chemical reactants, dyes, pigments, inks, etc.

As examples of medicaments, mention may be made of bactericides such as antiseptics and antibiotics, antiinflammatories, analgesics, local laxatives, hormones, proteins, etc.

As examples of cosmetic active principles, mention may especially be made of vitamins, sunscreens, antioxidants such as free-radical scavengers, for instance superoxide dismutase, fragrances, odor absorbers, deodorants, antiperspirants, dyes, pigments, emollients, moisturizers, etc.

As examples of chemical reactants, mention may especially be made of colored reactants, colored indicators such as pH indicators, catalysts, polymerization initiators, monomers, complexing agents, etc.

The substance or substances of interest may represent either the entirety or a portion of the balance to 100% of the fatty phase. The substance or substances of interest generally represent from 0.1% to 50% by weight approximately, and preferably from 0.1% to 25% by weight approximately of the total weight of the fatty phase.

The fatty phase may in addition contain one or more additives conventionally used in emulsions and among which mention may especially be made, by way of example, of protective agents or agents for preserving the substance of interest, such as antioxidants and UV stabilizers.

Another subject of the invention is a process for preparing the material as defined above. This process is characterized in that it comprises the following steps that consist:

1) in a first step, in bringing a fatty phase predominantly comprising a solid crystallizable oil (CO) having a melting point $T_M$ below 100° C. to a temperature $T_{CO}$ such that $T_{CO}$ is greater than $T_M$, in order to obtain a crystallizable oil in the liquid state;

2) in a second step, in incorporating into the fatty phase in the liquid state at least one substance of interest;

3) in a third step, in bringing said fatty phase in the liquid state into contact with an aqueous phase (AP) previously brought to a temperature $T_{AP}$ such that $T_{AP}$ is greater than $T_M$, said aqueous phase containing, in addition, colloidal solid particles;

4) in a fourth step, in subjecting the liquid mixture resulting from the third step to a mechanical stirring in order to obtain an oil-in-water emulsion formed of droplets of fatty phase in the liquid state dispersed in the continuous aqueous phase and in which the colloidal solid particles are present at the interface formed between the continuous aqueous phase and the dispersed fatty phase droplets;

5) in a fifth step, in bringing said O/W emulsion to a temperature $T_{O/W}$ such that $T_{O/W}$ is less than $T_M$ in order to give rise to the solidification of the fatty phase and to obtain an O/W emulsion formed of globules of fatty phase in the solid state, said globules being dispersed in the aqueous phase;

6) in a sixth step, in forming a shell comprising at least one silicium oxide around said globules by addition, to the aqueous phase of the emulsion, and with mechanical stirring, of at least one precursor of silicium oxide and of a sufficient amount of at least one acid in order to bring the aqueous phase to a pH of less than or equal to 4 in order to obtain said material; and 7) in a seventh step, in separating said material from the aqueous phase.

The colloidal solid particles present in the aqueous phase during the third step may be mineral or organic. Preferably, they are mineral particles. The colloidal solid particles are preferably mineral particles chosen from the group of metal oxides, hydroxides and sulfates. Among such oxides, mention may very particularly be made of silicon, titanium, zirconium and iron oxides, and also salts thereof such as silicates (for example clays). Finally, mention may be made of colloidal particles of carbon. Among the organic colloidal solid particles, mention may especially be made of polymeric particles, for example latex particles.

In order to be colloidal, the solid particles generally have a size of less than a few micrometers. Thus, the particles generally have an average size between 5 and 5000 nm, and preferably between 5 and 500 nm.

According to one particularly preferred embodiment of the invention, the colloidal solid particles are chosen from silicon oxide nanoparticles. By way of example, mention may especially be made of the products sold under the trade name Aerosil® by the company Evonik Degussa.

The amount of colloidal solid particles generally varies from 0.01% to 10%, in particular from 0.1% to 5% by weight relative to the total weight of the fatty phase. Advantageously, the amount of colloidal solid particles present in the continuous aqueous phase varies as a function of the volume-average size of the desired droplets of the fatty phase in the emulsion, the average diameter of which varies from 1 µm to 1 cm, preferably between 5 and 500 µm, and more preferably still between 10 and 200 µm approximately.

Furthermore, the colloidal solid particles generally have a hydrophilic and charged surface, which does not favor their absorption at the surface of the droplets of the dispersed fatty phase.

Thus, and according to one preferred embodiment of the invention, the colloidal solid particles are surface-functionalized in order to favor their adsorption at the interface formed between the continuous aqueous phase and the dispersed fatty phase droplets.

The colloidal solid particles may thus be functionalized by compounds bonded to their surface via covalent bonds. This may be carried out by pretreatment of the particles, in particular by chemical grafting of a compound comprising hydrophobic groups such as a trialkoxysilane of formula R—Si—(OR')$_3$, in which R is an linear or branched $C_1$ to $C_{12}$, in particular $C_2$ to $C_{10}$ alkyl, very particularly n-octyl, optionally bearing an amino group and R', which is identical to or different from R, is a linear or branched $C_1$ to $C_{12}$, in particular $C_1$ to $C_6$ alkyl group, and very particularly ethyl.

The colloidal solid particles may also be functionalized via adsorption of surfactant molecules at their surface which make it possible to give them a certain hydrophobicity, the hydrophilic end of the surfactant being adsorbed on the surface of the particles. The surfactants that can be used for functionalizing the particles are preferably cationic or anionic surfactants.

Among these surfactants, sodium alkyl sulfates such as, in particular, sodium dodecyl sulfate (SDS) and alkyltrimethylammonium bromides are particularly preferred.

The surfactant is preferably chosen from surfactants having a charge opposite to that of the surface of the colloidal solid particles. This choice makes it possible to favor the adsorption of the surfactant at the surface of the particles.

By way of example of surfactant-functionalized particles, mention may especially be made of the silica nanoparticles, the surface of which is functionalized by a quaternary ammonium such as those sold under the name Aerosil® A380 by the company Evonik Degussa, having a diameter of 7 nm, and the surface of which is functionalized by cetyltrimethylammonium bromide (CTAB).

The functionalization of the colloidal solid particles by a surfactant may also be carried out in situ, that is to say during their introduction into the continuous aqueous phase of the emulsion. In this case, the continuous aqueous phase of the emulsion also contains said surfactant in an amount preferably below the critical micelle concentration (CMC), this surfactant then being adsorbed at the surface of the particles when these are in the aqueous phase of the emulsion. Preferably, the amount of surfactant varies from $1/200^{th}$ to $1/3$ of the CMC.

The continuous aqueous phase mainly comprises water and optionally an alcohol, such as methanol, ethanol, isopropanol or butanol, preferably ethanol.

The mechanical stirring carried out during the fourth step may especially be carried out in a device designed for emulsifying, such as, for example, in devices sold under the trade names Ultra-Turrax® or Rayneri®.

The size distribution of the droplets of the fatty phase in the O/W emulsion is generally narrow (U<40%).

During the sixth step, the addition of at least one silicium oxide precursor at acid pH gives rise to the condensation of said precursor at the interface of the globules of fatty phase in the solid state and the formation of the shell.

The silicium oxide precursors may be chosen from silicium alkoxides and in particular from tetramethoxyorthosilane (TMOS), tetraethoxyorthosilane (TEOS), dimethyldiethoxysilane (WADES), (3-mercaptopropyl)trimethoxysilane, (3-aminopropyl)triethoxysilane, N-(3-trimethoxysilylpropyl)pyrrole, 3-(2,4-dinitrophenylamino)propyltriethoxysilane, N-(2-aminoethyl)-3-aminopropyltrimethoxysilane, phenyltriethoxysilane, methyltriethoxysilane and mixtures thereof. Among these precursors, TEOS is particularly preferred. These precursors may be substituted, completely or partially, by silicate sols.

The thickness of the shell depends on the amount of silicium oxide precursors used during the sixth step and on the diameter of the dispersed fatty phase globules. This amount is expressed relative to the total surface area in $m^2$ of the dispersed phase globules of the emulsion.

According to one preferred embodiment of the invention, the amount of silicium oxide precursor varies from 0.05 to 4 $M/m^2$, and more preferably still from 0.2 to 2.2 M per $m^2$ of surface area of the dispersed phase globules of the emulsion.

To achieve the highest thicknesses of the shell, the sixth step may be carried out several times until the desired thickness is obtained.

When the shell of the material in accordance with the invention comprises, besides silicium oxide, a metal oxide, at least one precursor of a metal oxide of formula $MeO_2$ is then also added to the aqueous phase of the emulsion, said precursor being chosen from alkoxides, chlorides or nitrates of metals chosen from Zr, Ti, Th, Nb, Ta, V, W and Al.

When they are used, the amount of these precursors of metal oxide of formula $MeO_2$ varies from 0.001 M to 1 M, and preferably from 0.01 to 0.6 M per $m^2$ of surface area of the dispersed phase globules of the emulsion.

The pH of the aqueous phase during the sixth step preferably varies from 0.01 to 4, and more preferably still from 0.1 to 2.1.

The acid used to adjust the pH of the aqueous phase may be chosen from mineral and organic acids, among which mention may in particular be made of hydrochloric acid, acetic acid, nitric acid and sulfuric acid.

During the seventh step, the material in accordance with the invention may be separated from the aqueous phase and recovered by any conventional separation technique known to a person skilled in the art, such as filtration, centrifugation and the use of screens. It is then preferably washed, for example, with water, then dried for example by lyophilization in order to give a powder.

The material thus obtained is stable during storage for several months on condition that the storage temperature is below the temperature $T_M$ of the fatty phase confined in the shell.

The material in accordance with the invention may be used in the form of powder or dispersion in a solvent in order to deliver the substance or substances of interest present in the solid fatty phase confined in the shell based on silicium oxide.

Another subject of the invention is therefore the use of a material in accordance with the invention and as described previously for the thermostimulated delivery of at least one substance of interest.

The delivery of the substance of interest is obtained by rupture of the shell under the effect of a rise in temperature to a delivery temperature $T_D$ such that $T_D > T_M$.

By way of example, and when the substance of interest is a medicament, the crystallizable oil present in the fatty phase is preferably chosen from the crystallizable oils having a melting point below 37° C. Thus, when said material is incorporated into a pharmaceutical composition and when this composition is administered to a patient, for example orally, the composition ingested will find itself at body temperature, in general 37° C. or above, which will lead to the melting of the fatty phase and its volume expansion and thus the rupture of the silica shell and the delivery of the medicament.

According to another example, the substance of interest is a cosmetic active principle and the material is part of the components of a cosmetic composition for topical application, such as a powder, a cream or a gel. The heating of the fatty phase of the material to a temperature above $T_M$ may in this case be produced by a local rubbing during the spreading of the cosmetic composition, which induces a local heating leading to the rupture of the shell and the local release of the substance of interest. If the cosmetic composition is in the form of a powder, its application via spreading may be accompanied by a change in texture (conversion of the powder to a composition having a greasy feel due to the rupture of the shell).

As other examples of the use of the material in accordance with the invention, mention may especially be made of:

the use as a storage control for an article, for example for a food contained in a food packaging, at a temperature below a maximum storage temperature. In this case, the food packaging comprises a storage control containing a material in accordance with the invention in which the fatty phase contains a reactant, the color of which changes or is revealed during the rupture of the shell by exposure of the packaging to a temperature above the maximum storage temperature of the food, the crystallizable oil of the fatty phase being chosen from oils having a melting point just above the maximum storage temperature;

use for delivering a fragrance into the air (deodorizing action), into a textile, onto the skin, etc., as soon as the temperature of the air, of the textile or of the skin reaches a value above the melting point of the fatty phase;

use for delivering an initiator of a polymerization reaction induced by rise in temperature;

use for the thermostimulated delivery of a reactant during a chemical reaction;

use for the delivery of a bactericidal agent into an industrial installation, for example into a ventilating duct or air-conditioning duct, when the temperature of the installation reaches the proliferation temperature of the bacteria;

use for the storage of molecules of interest, etc.

Another subject of the invention is the use of the material as described above, as an ingredient for the preparation of pharmaceutical, cosmetic or food products, and also the pharmaceutical, cosmetic or food products containing, as an ingredient, at least one material in accordance with the invention.

These compositions may contain the conventional pharmaceutical, cosmetic or food supports that are well known to a person skilled in the art, and also one or more surfactants intended to favor the release of the liquid fatty phase during the rupture of the capsule.

DETAILED DESCRIPTION

Figure 1:
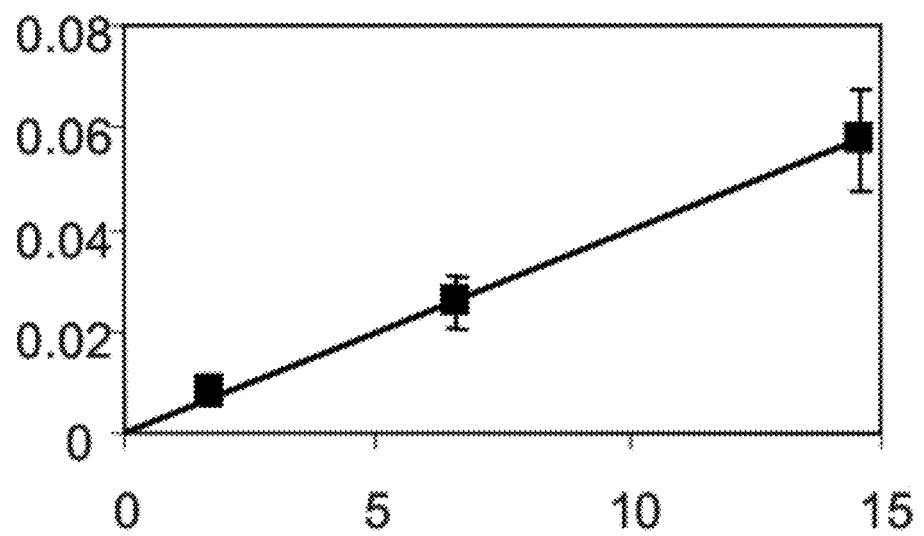
FIG. 1 represents the inverse of the average diameter of the particles of the material of Example 1, in accordance with one embodiment.

The present invention is illustrated by the following exemplary embodiments, to which it is not however limited.

EXAMPLES

The raw materials used in the examples that follow are listed below:

paraffins together having a melting range from 42 to 44° C. or from 46 to 48° C. (CAS No.: 8002-74-2), both sold by the company Merck;

99% pure eicosane (melting point=37° C.) sold by the company Aldrich;

Suppocire® DM, suppository excipient, composed of a mixture of triglycerides, the melting points of which extend from 27 to 48° C., sold by the company Gattefossé.

tetraethoxyorthosilane (TEOS) and cetyltrimethylammonium bromide (CTAB), Fluka;

silica nanoparticles having a diameter of 7 nm, sold under the name Aerosil® A380 by the company Evonik Degussa;

sodium dodecyl sulfate (SDS), from Aldrich;

nonionic surfactant consisting of a mixture of $C_{12}$ and $C_{10}$ polyoxyethylenes containing 5 mol of ethylene oxide, supplied under the name Ifralan® D205 by the company IfraChem.

These raw materials was used as received from the manufacturers, without additional purification.

The materials obtained were characterized using an inverted optical microscope sold under the trade name Axiovert® X100 by the company Zeiss and equipped with a heating stage from the company Mettler making it possible to control the temperature and also the heating and cooling rates.

The size distribution of the emulsions was studied using a particle size analyzer sold under the trade name Mastersizer Hydro MS2000 by the company Malvern Instrument. The particle size measurements were carried out at 25° C. in pure water. The intensity of the scattering, as a function of the angle, which was collected was converted using Lorenz-Mie theory. The size distribution of the particles was expressed by their weighed average diameter (D) and their polydispersity (P) by applying equations (1) and (2) below:

$$D = \frac{\sum_i N_i D_i^3}{\sum_i N_i D_i^2} \text{ and} \tag{1}$$

$$P = \frac{1}{\overline{D}} \frac{\sum_i N_i D_i^3 |\overline{D} - D_i|}{\sum_i N_i D_i^3} \tag{2}$$

in which:

$D_i$ is the diameter of the particles, $N_i$ is the total number of droplets of diameter $D_i$, $\overline{D}$ is the median diameter, that is to say the theoretical opening of the screen such that 50% of the particles, by weight, have a larger diameter and 50% a smaller diameter.

These formulae are applied to the particle size analyzers from the company Malvern Instrument.

At the temperatures at which the measurements were made, the droplets were solid and of substantially spherical shape.

The materials were observed using a scanning electron microscope (SEM) sold under the reference TM-1000 by the company Hitachi. In order to obtain a better resolution and to estimate the thickness of the silica cell, the samples were also observed by SEM using scanning microscopes sold under the references Jeol JSM-840A and Jeol 6700F. In order to do this, the particles were first either dried at room temperature, or lyophilized using a lyophilizing machine sold under the name Alpha 2-4 LD Plus from the company Christ. All the particles were covered with gold before being observed by SEM.

EXAMPLES

Example 1

Preparation, Characterizations and Study of Materials in Accordance with the Invention In this example, the preparation, characterization and study of materials in accordance with the invention, constituted of a silica shell containing a crystallizable oil, are illustrated.

1) Preparation of the Materials i) First Step: Functionalization of the Silica Particles 1.38 g of Aerosil® A380 silica nanoparticles were dispersed in 300 ml of distilled water, using an ultrasonic bath. Added next to this dispersion were 24 mg of (CTAB, this amount representing around $\frac{1}{5}^{th}$ of the critical micelle concentration (CMC=$0.9 \times 10^{-3}$ mol/l). Since the surface of the silica nanoparticles is negatively charged, the CTAB (cationic surfactant) is adsorbed at the surface of the silica particles and thus makes it possible to give them an amphiphilic character. An aqueous phase containing a dispersion of surface-functionalized silica nanoparticles was obtained.

ii) Second Step: Preparation of the Emulsions

Depending on the emulsions, the compositions of which are specified in table 1 below, a given amount of the dispersion of functionalized silica nanoparticles obtained above in the preceding step was diluted with water. This aqueous phase was heated at a temperature of 65° C., then variable amounts of crystallizable oil as listed in table 1 (paraffin 42-44; paraffin 46-48 or eicosane), previously brought to a liquid state by heating, were introduced into the dispersion of silica nanoparticles with vigorous stirring using a stirrer sold under the name Ultra-Turrax® 125 by the company Janke & Kunkel, equipped with a dispersion tool S25, finishing with stirring at 9000 rpm for 1 minute. The emulsions were then left to return to room temperature, without stirring. After cooling of the emulsions to a temperature below the melting point of the crystallizable oil, CTAB was added in an amount sufficient to attain the critical micelle concentration in order to prevent the aggregation of the wax particles and to enable storage of the emulsions.

iii) Third Step: Formation of the Silica Shell

In this step, the formation of the silica shell around the wax particles was carried out.

The emulsions of wax particles were diluted to 7% by weight and the pH of the emulsions was adjusted to around 0.2, that is to say to a value below the isoelectric point of the silica, by addition both of a solution of hydrochloric acid at 37% by volume and of a solution containing 1% by weight of CTAB. These emulsions were distributed into 10 ml test tubes.

The TEOS was then added dropwise to the emulsions in order to attain the quantity noted in table 1, i.e. 1 M of TEOS per $m^2$ of surface area of stabilized wax particles for the emulsions $E_{0.17}$, $E_{0.67}$, $E_{1.45}$ and $P_{42-44}$ and 1.7 M/m$^2$ of surface area of stabilized wax particles for the emulsion $P_{46-48}$.

The silica shell was then left to form (mineralization) with continuous stirring on the wheel at 25 rpm in a chamber thermostatediy controlled at 25° C.

At the end of the mineralization, the silica particles were recovered by centrifugation and washed several times with distilled water. The material obtained was stored in pure water for several months. No deterioration of the capsules was observed over this period.

2) Results of the Characterizations

The appended FIG. 1 represents the inverse of the average diameter of the particles of the material in accordance with the invention as a function of the ratio between the amount of functionalized silica particles and the weight of eicosane used during the preparation of the emulsions (step ii). In this figure, the inverse of the average diameter (D) of the particles in $\mu m^{-1}$ (1/D) is a function of the weight ratio between the weight of functionalized silica particles (in mg) over the weight of eicosane (in g).

Figure 2:
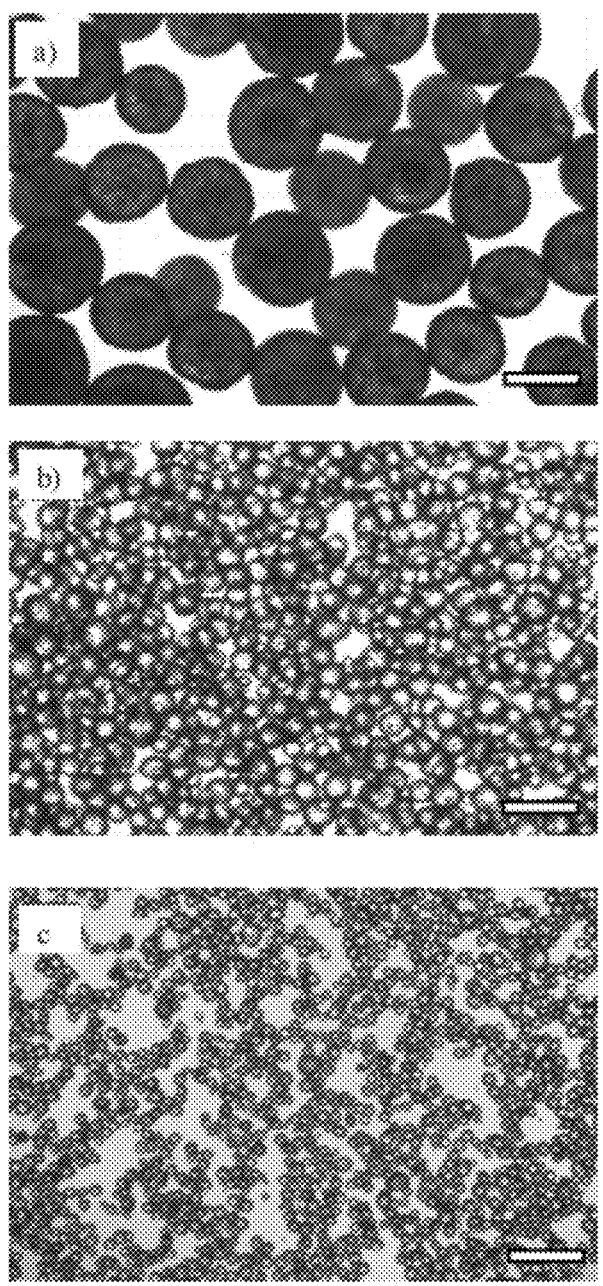
FIGS. 2a-2c show optical microscopy images of emulsions of eicosane in water from Example 1, in accordance with one embodiment.

The appended FIG. 2 shows optical microscopy images of emulsions of eicosane in water obtained with various functionalized silica particles/eicosane weight ratios; FIG. 2a: $E_{0.17}$; FIG. 2b: $E_{0.67}$ and FIG. 2c: $E_{1.45}$% by weight. In FIGS. 2a, 2b and 2c, the scale bar corresponds to 100 μm.

Figure 3:
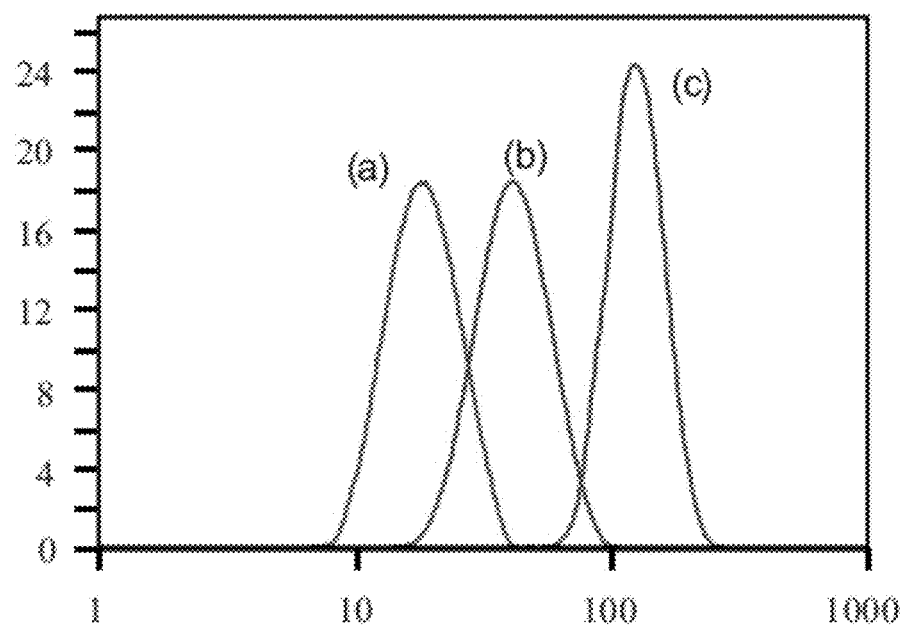
FIG. 3 represents the particle size distribution of the particles of the three emulsions presented in the images from FIG. 2.

The appended FIG. 3 represents the particle size distribution of the particles of the three emulsions presented in the images from FIG. 2: (a)=$E_{0.17}$, (b)=$E_{0.67}$ and (c)=$E_{1.45}$ and for which the respective average diameters are 17.4 μm (a), 39 μm (b) and 121 μm (c) and the respective polydispersity indices are 0.26 (a), 0.26 (h) and 0.19 (c). In this figure, the cumulative volume of the particles of the emulsion, having comparable diameters, is reported (in %) as a function of the diameter of the particles (in μm) (particle size distribution, by volume, of the particles). FIG. 3 represents the particle size distribution curves of the three emulsions (a), (b) and (c).

The results presented in these figures show that the preparation process in accordance with the present invention results in emulsions in which the particle size distribution of the particles is narrow (low polydispersity). FIG. 3 shows that

TABLE 1

| Emulsion | Nature of the oil | $Q_O$: quantity of oil (in g) | $Q_{AP}$: quantity of aqueous phase (in g) | $Q_{SP}$: quantity of silica particles (in mg) | $Q_{SP}/Q_O$ weight ratio (g/g) | Quantity of CTAB (in mg) | Quantity of TEOS (in M/m$^2$) |
|---|---|---|---|---|---|---|---|
| $E_{0.17}$ | Eicosane | 12.36 | 78.00 | 21 | 0.0017 | 0.37 | 1 |
| $E_{0.67}$ | Eicosane | 12.36 | 78.00 | 83 | 0.0067 | 1.44 | 1 |
| $E_{1.45}$ | Eicosane | 12.36 | 78.00 | 180 | 0.0145 | 3.12 | 1 |
| $P_{42-44}$ | Paraffin 42-44 | 12.36 | 77.00 | 180 | 0.0133 | 3.12 | 1 |
| $P_{46-48}$ | Paraffin 46-48 | 12.36 | 78.00 | 180 | 0.0145 | 3.12 | 1.7 | particles having an average diameter that varied between about ten and a few hundred of μm were obtained.

Figure 4:
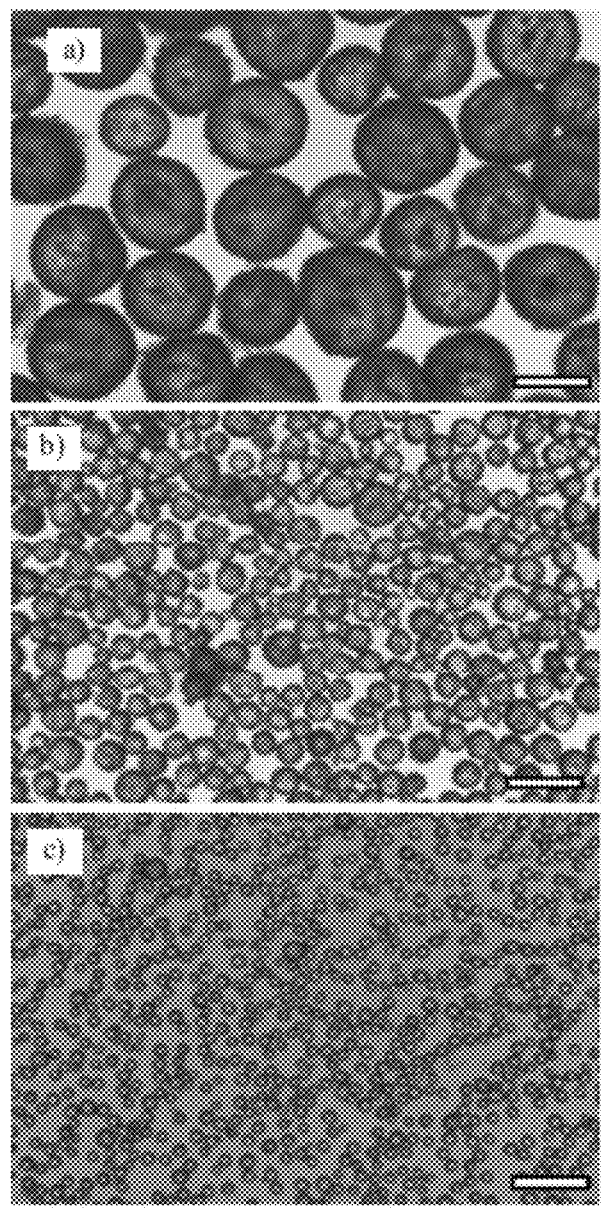
FIGS. 4a-4c represent optical microscopy images of the material obtained by mineralization of the eicosane emulsions (a), (b) and (c) stabilized by functionalized silica particles of FIG. 3.
Figure 5:
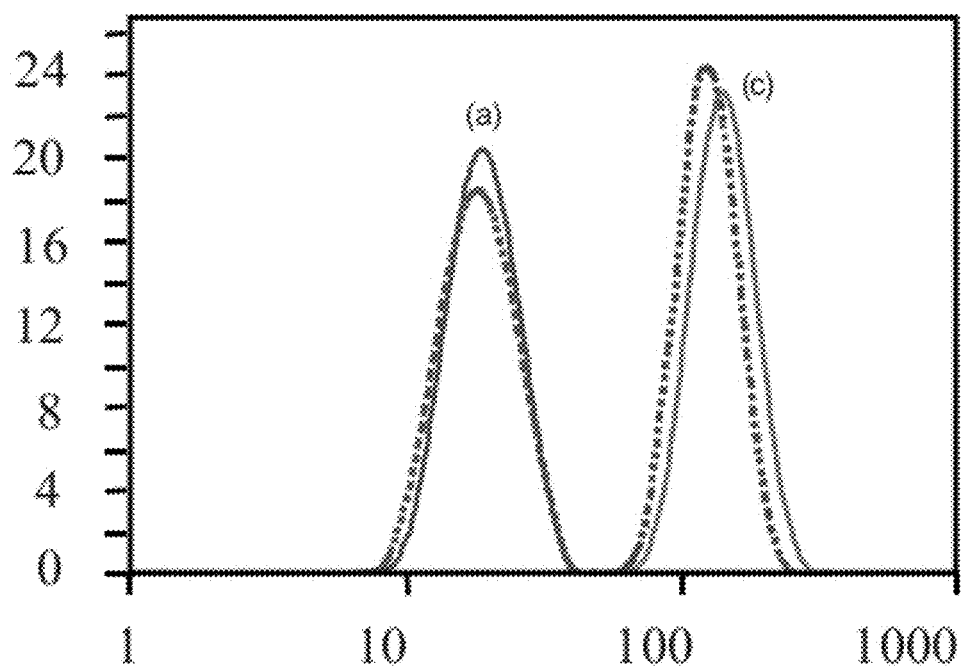
FIG. 5 represents the particle size distribution curves of emulsions (a) and (c) from FIG. 3, before (dotted-line curves) and after (continuous-line curves) mineralization.

The appended FIG. 4 represents optical microscopy images of the material Obtained by mineralization of the eicosane emulsions (a), (b) and (c) stabilized by functionalized silica particles of FIG. 3. In these figures, the scale bar represents 100 μm. The appended FIG. 5 represents the particle size distribution curves of emulsions (a) and (c) from FIG. 3, before (dotted-line curves) and after (continuous-line curves) mineralization. In this figure, the cumulative volume of the particles of the emulsion, having comparable diameters, is reported (in %) as a function of the diameter of the particles (in μm). AU of the results presented in FIGS. 4 and 5 show that the mineralization step does not broaden the particle size distribution and that it does not lead to agglomeration of the particles.

Figure 6:
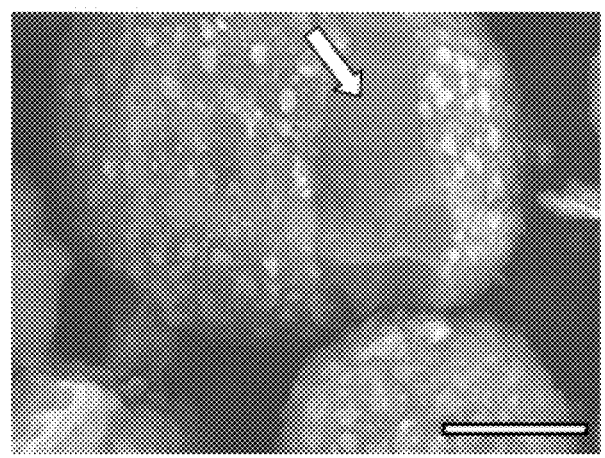
FIG. 6 is an SEM photograph taken during the observation of a material in accordance with one embodiment from example 1 obtained by mineralization of the emulsion $P_{46-48}$.

FIG. 6 is an SEM photograph taken during the observation of a material in accordance with the invention obtained by mineralization of the emulsion $P_{46-48}$. This photograph was obtained after rupture of the shell by a rise in temperature due to the focusing of the electron beam on the capsules. In this figure, the scale bar represents 10 μm and the white arrow points to the fracture zone caused by the expansion of the wax.

Figure 7:
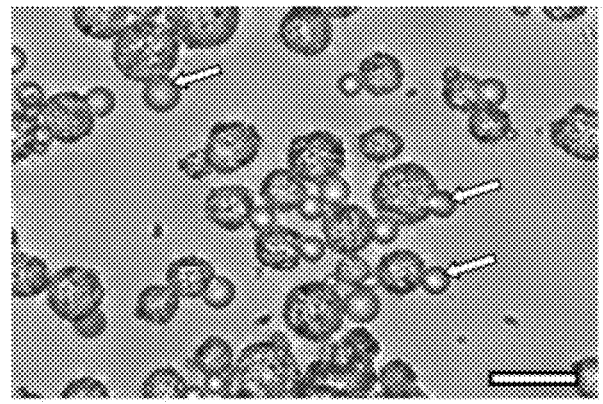
FIG. 7 is an optical microscopy image of the emulsion $F_{0.67}$ from FIG. 3b, in which the white arrows show the droplets of eicosane released into the water following the rupture of the shell.

The emulsion $E_{0.67}$ from FIG. 3b) was then observed by optical microscopy using the microscope with a Mettler heating stage in order to study the rupture of the silica shell under the effect of the rise in temperature to a temperature above 37° C., that is to say to a temperature above the melting point of eicosane. The corresponding image is given by appended FIG. 7, in which the white arrows show the droplets of eicosane released, into the water following the rupture of the shell; the scale bar corresponds to 60 μm.

Figure 8:
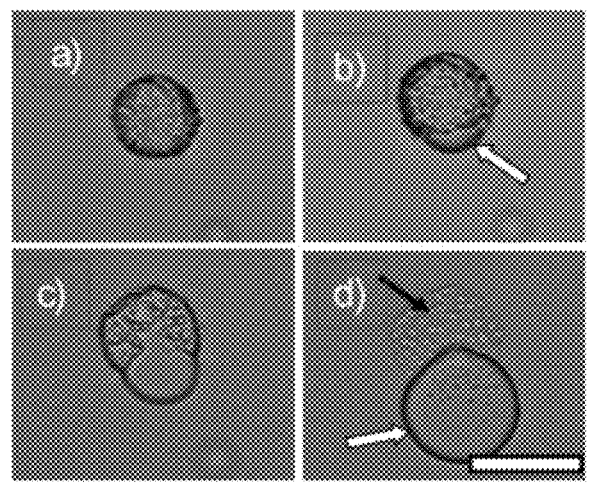
FIGS. 8a-8d are optical microscopy images of the emulsion $P_{42-44}$ while being subjected to a rise in temperature.

The emulsion $P_{42-44}$ was also observed by optical microscopy while being subjected to a rise in temperature at a rate of 5° C. per min up to a temperature of 60° C. The corresponding images are given by appended FIG. 8 in which the image 8a) corresponds to the photograph taken at 35° C. (temperature below the melting point of paraffin 42-44), image 8b) corresponds to the photograph taken at 50° C. (temperature above the melting point of paraffin 42-44), image 8c) corresponds to the photograph taken at 55° C. and photo 8d) corresponds to the photograph taken at 60° C. In this figure, the scale bar corresponds to 20 μm, the white arrows show the drop of oil leaving the silica shell, the black arrow shows the empty silica shell after release of the oil. This figure shows that when the temperature becomes higher than the melting point of the crystallizable oil contained inside the silica shell, the rupture of the shell is observed, which is caused by the thermal expansion of the oil, thus enabling its release.

Figure 9:
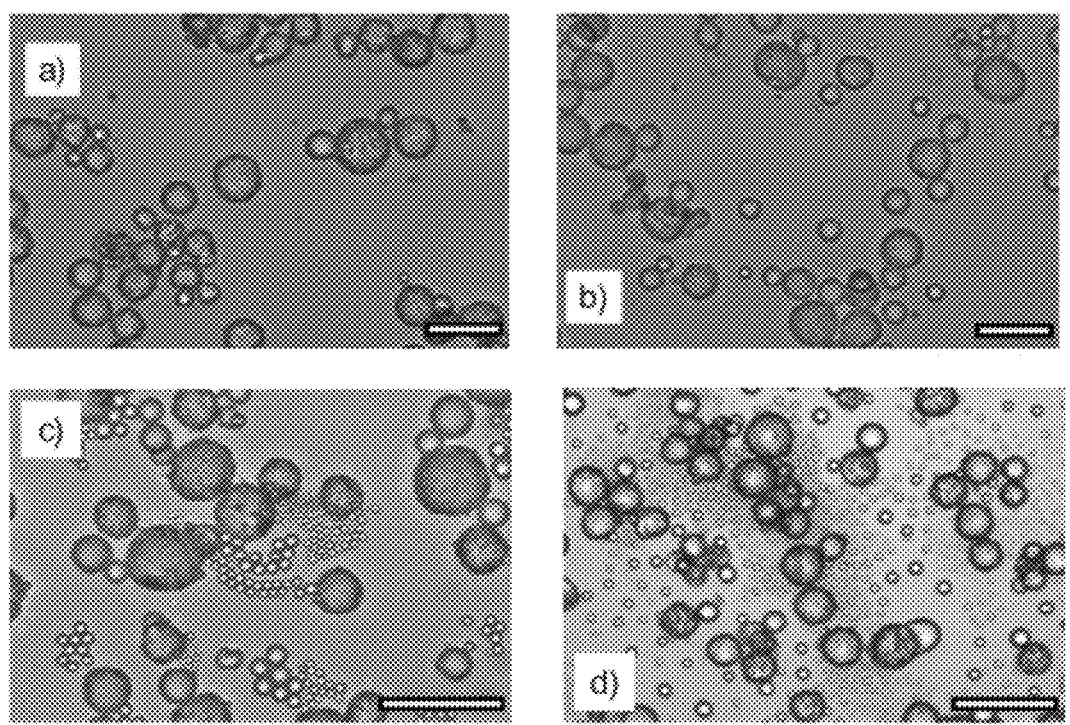
FIGS. 9a-9d are optical microscopy images showing the effects of the presence of various surfactants on the release of the oil obtained by mineralization of the emulsion $E_{0.67}$.

Finally, the effects of the presence of various surfactants (in an amount sufficient to attain 60 times the critical micelle concentration) on the release of the oil were also studied by the material obtained by mineralization of the emulsion $E_{0.67}$. The corresponding results are given in the appended FIG. 9, which represents optical microscopy images of the release of the eicosane droplets after heating from 33 to 53° C. at a rate of temperature rise of 5'C/min, during the release of eicosane without addition of surfactant (FIG. 9a), in the presence of an anionic surfactant: SDS (FIG. 9b), in the presence of a cationic surfactant: CTAB (FIG. 9c) or in the presence of a nonionic surfactant: Ifralan® D205 (FIG. 9d). In this figure, the scale bar corresponds to 60 μm.

The presence of a surfactant promotes even more the release of the oil in the form of even smaller droplets since it lowers the interfacial tension between water and the oil. It is known that the interfacial tension between a liquid oil such as octane and water is equal to around 0.75 mN/m in the presence of Ifralan D205 at a concentration above its CMC, is equal to around 3.81 mN/m in the presence of CTAB at a concentration above its CMC, and is equal to around 10 mN/m in the presence of SDS at a concentration above its CMC.

The addition of stirring or a hydrodynamic flow favors the detachment of the oil from the silica shell.

It is thus possible to vary the size of the oil droplets and the method of release as function of the presence or absence of surfactant in the medium surrounding the material in accordance with the invention during the rupture of the silica shell.

Example 2

Preparation of a Particulate Material Constituted of a Suppocire® DM Core and a Silica Shell In this example, the preparation, characterization and study of the material in accordance with the invention, constituted of a silica shell containing a biocompatible oil constituted of a mixture of triglycerides and sold under the name Suppocire® DM by the company Gattefossé are illustrated.

The protocol used for the preparation of the materials prepared above in example 1 was used in this example, using the following components:

Suppocire® DM: 12.4 g
Aqueous phase: 87.00 g
Functionalized silica particles as prepared in example 1: 0.046 g
Quantity of particles/quantity of oil weight ratio: 0.0037
CTAB: 0.008 g
TEOS: 1 M/m².

Figure 10:
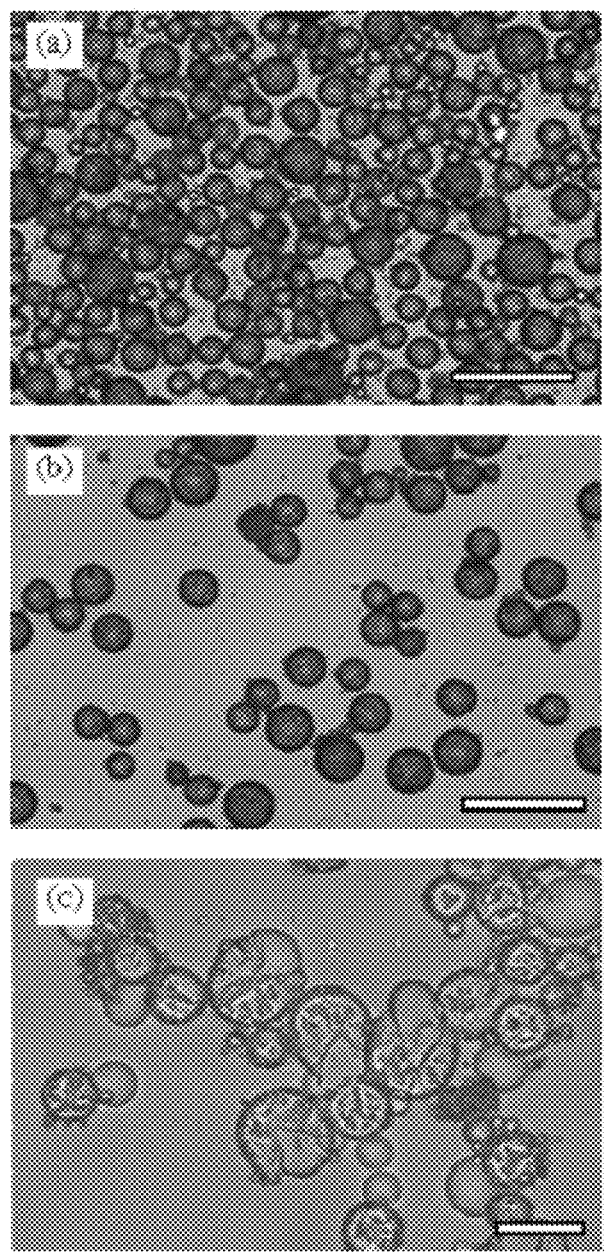
FIGS. 10a-10c are optical microscopy images from Example 2 of a) the Suppocire® DM emulsion, b) the material obtained after mineralization and c) capsules during the raising of the temperature to a temperature of 55° C.

The appended FIG. 10 presents optical microscopy images of a) the Suppocire® DM emulsion, b) the material obtained after mineralization and c) capsules during the raising of the temperature to a temperature of 55° C. In these photographs, the scale bar represents 60 μm.

What is claimed is:

1. A material in the form of a powder of either one of or both spherical or substantially spherical solid particles comprising:
    a continuous solid shell of a thickness of 0.1 to 2 μm that includes at least one silicium oxide,
    wherein said solid shell forms a capsule that encapsulates at least one fatty phase,
    wherein said fatty phase is solid at the storage temperature of said material and predominantly comprises a crystallizable oil chosen from fatty substances and mixtures of fatty substances, of natural or synthetic origin, the melting point of which is above 15° C. and having a melting point $(T_M)$ below 100° C. and at least one substance of interest,
    the diameter of said particles varies from 1 μm to 1 cm,
    wherein the substance of interest is selected from the group consisting of medicaments, active principles that can be used in cosmetics, chemical reactants, dyes, pigments and inks.

2. The material as claimed in claim 1, wherein said melting point varies from 20 to 50° C.

3. The material as claimed in claim 1, wherein the crystallizable oil represents 50% to 99.9% by weight of the fatty phase.

4. The material as claimed in claim 1, wherein the crystallizable oil is selected from the group consisting of paraffins, triglycerides; fatty acids; rosins; waxes; hydrogenated plant oils and also mixtures thereof; synthetic bitumens; and mixtures thereof.

5. The material as claimed in claim 1, wherein the diameter of the particles varies from 5 am to 500 μm.

6. The material as claimed in claim 1, wherein the silica solid shell also comprises one or more metal oxides of formula $MeO_2$ in which Me is a metal selected from the group consisting of Zr.

7. The material as claimed in claim 1, wherein the substance of interest is medicaments.

8. The material as claimed in claim 1, wherein the substance or substances of interest represent from 0.1% to 50% by weight of the total weight of the fatty phase.

9. The material as claimed in claim 1, wherein said material is structured as a powder, for the thermostimulated delivery of at least one substance of interest.

10. The material as claimed in claim 1, wherein the thermostimulated delivery is obtainable by rupture of the silica solid shell under the effect of a rise in temperature to a delivery temperature $T_D$ such that $T_D > T_M$.

11. The material as claimed in claim 1, wherein said material is structured to be applicable as an ingredient for the preparation of pharmaceutical.

12. The material as claimed in claim 1, wherein said material is a Pharmaceutical.

* * * * *

UNITED STATES PATENT AND TRADEMARK OFFICE
CERTIFICATE OF CORRECTION

PATENT NO. : 9,017,706 B2  
APPLICATION NO. : 13/387758  
DATED : April 28, 2015  
INVENTOR(S) : Schmitt et al.

Page 1 of 1

It is certified that error appears in the above-identified patent and that said Letters Patent is hereby corrected as shown below:

In the Claims

Column 13, Claim 5, Line 5: "5 am" should read as "5 um"

Signed and Sealed this
Eighteenth Day of August, 2015

Michelle K. Lee
*Director of the United States Patent and Trademark Office*